US005725870A

United States Patent [19]
Thoene

[11] Patent Number: 5,725,870
[45] Date of Patent: Mar. 10, 1998

[54] METHODS, COMPOSITES AND ARTICLES FOR CONTRACEPTION

[76] Inventor: Jess G. Thoene, 1308 Brooks St., Ann Arbor, Mich. 48103

[21] Appl. No.: 585,100

[22] Filed: Jan. 16, 1996

Related U.S. Application Data

[63] Continuation-in-part of Ser. No. 492,478, Jun. 22, 1995, Pat. No. 5,646,189, which is a continuation of Ser. No. 136,697, Oct. 15, 1993, abandoned.

[51] Int. Cl.$^6$ .................................. A61F 6/06; A61L 9/04
[52] U.S. Cl. .......................... 424/433; 424/45; 424/430; 514/967
[58] Field of Search ........................... 424/45, 430, 433; 514/967

[56] References Cited

U.S. PATENT DOCUMENTS

| | | |
|---|---|---|
| 3,892,824 | 7/1975 | Piper et al. . |
| 3,991,190 | 11/1976 | Garzia et al. . |
| 5,260,054 | 11/1993 | Nandagiri et al. . |
| 5,362,487 | 11/1994 | Nandagiri et al. ..................... 424/71 |
| 5,554,655 | 9/1996 | Thoene . |

FOREIGN PATENT DOCUMENTS

| | | |
|---|---|---|
| 1 157 774 | 11/1983 | Canada . |
| 0 174 912 A2 | 9/1985 | European Pat. Off. . |
| 204989 | 12/1986 | European Pat. Off. . |
| WO 90/08540 | 8/1990 | WIPO . |
| WO 90/14007 | 11/1990 | WIPO . |
| WO 93/06832 | 4/1993 | WIPO . |
| WO 94/04185 | 3/1994 | WIPO . |

OTHER PUBLICATIONS

*Fields Virology*, 2nd Ed., B.N. Fields et al, Eds., Raven Press, NY, vol. 1, pp. 1075–1089 (1990).
*Fields Virology*, 2nd Ed., B.N. Fields et al, Eds., Raven Press, NY, vol. 2 pp. 1437–1440, 1452–1477 (1990).
*Fields Virology*, 2nd Ed., B.N. Fields et al, Eds., Raven Press, NY, vol. 1, pp. 507–548 (1990).
*Fields Virology*, 2nd Ed., B.N. Fields et al, Eds., Raven Press, NY, vol. 2, pp. 1787–1790 (1990).
*Fields Virology*, 2nd Ed., B.N. Fields et al, Eds., Raven Press, NY, vol. 2, pp. 1529–1543 (1990).
Dagani, C&EN, Nov. 23, 1987, pp. 41–49.
Droge et al, *Am. J. Med.*, vol. 91, pp. 140S–144S (1991).
Mihm et al, *AIDS*, vol. 5, pp. 497–503 (1991).
Perrin et al, *Pharmac. Ther.*, vol. 12, pp. 255–297 (1981).
Pompei et al, *Experientia*, vol. 33, pp. 1151–1152 (1977).
La Colla et al, *Ann. NY Acad. Sci.*, vol. 284, pp. 294–304 (1977).
La Colla et al, *Experientia*, vol. 31, pp. 797–798 (1975).
Marcialis et al, *Experientia*, vol. 29, pp. 1559–1661 (1973).
Schivo et al, *Experientia*, vol. 32, pp. 911–913 (1976).
Billard et al, *Antimicrobial Agents and Chemotherapy*, vol. 5, pp. 19–24 (1974).
Marcialis et al, *Experientia*, vol. 30, pp. 1272–1273 (1974).
Staal et al, *The Lancet*, vol. 339, pp. 909–912 (1992).

Roederer et al, *Proc. Natl. Acad. Sci. USA*, vol. 87, pp. 4884–4888 (1990).
Oxford et al, *J. Gen. Virol.*, vol. 18, pp. 11–19 (1973).
Oxford et al, *Ann. NY Acad.*, vol. 284, pp. 613–623 (1977).
Arora et al, *Can. J. Biochem.*, vol. 58, pp. 67–72 (1980).
Pisoni et al, *J. Bio. Chem.*, vol. 260, No. 8, pp. 4791–4798 (1985).
Thoene et al, *J. of Ped.*, vol. 96, No. 6, pp. 1043–1044 (1980).
Thoene et al, *J. Clin. Invest.*, vol. 58, pp. 180–189 (1976).
Gliniak et al, *J. Bio. Chem.*, vol. 226, No. 34, pp. 22991–22997 (1991).
Leonard et al, *J. Bio. Chem.*, vol. 265, No. 18, pp. 10373–10382 (1990).
Lekutis et al, *J. Acq. Imm. Def. Syn.*, vol. 5, pp. 78–81 (1992).
Papadopulos–Eleopulos et al, *The Lancet*, vol. 338, pp. 1013–1014 (1991).
Cardin et al, *J. Bio. Chem.*, vol. 266, No. 20, pp. 13355–13363 (1991) (ABSTRACT).
Kim et al, *Biochem. Biophys. Res. Comm.*, vol. 179, No. 3, pp. 1614–1619 (1991).
Gahl et al, *New Engl. J. Med.*, vol. 316, pp. 971–977 (1987).
Wilson et al, *J. Am. Chem. Coc.*, vol. 102, pp. 359–363 (1980).
Smolin et al, *Ped. Res.*, vol. 23, No. 6, pp. 616–620 (1988).
Owens et al, *Virology*, vol. 179, pp. 827–833 (1990).
Willey et al, *Proc. Natl. Acad. Sci. USA*, vol. 85, pp. 9580–9584 (1988).
Dedera et al, *J. Vir.*, vol. 65, No. 11, pp. 6129–6136 (1991).
Harakeh et al, *Am. Clin. Nutr.*, vol. 54, pp. 1231S–1235S (1991).
Bacq, *Chemical Protection Against Radiation*, IV pp. 16–35, Charles C. Thomas, USA.
Thoene, "Orphan Drugs and Orphan Diseases: Clinical Realities and Public Policy", pp. 125–131, Alan R. Liss, Inc., NY (1983).
Thoene, "Cooperative Approaches to Research and Development of Orphan Drugs", pp. 157–162, Alan R. Liss, Inc., (1985).
Turner, *Med. J. Austral.*, vol. 153, pp. 502 (1990).
Bergamini et al, *J. Clin. Invest.*, vol. 93, pp. 2251–2257 (1994).
Ryser et al, *Proc. Natl. Acad. Sci. USA*, vol. 91, pp. 4559–4563 (1994).
Schroeder et al, *Chemical Abstracts* 110:18156e (1989).
Hotz et al, *Chemical Abstracts*, 81:101420q (1974).
Thoene, *Clinical Research*, vol. 40, p. 246A Apr. 1992.
Cohen, *Science*, vol. 260, pp. 1712–1713 (1993).
Sarin et al, *Chemical Abstracts*, 107:108862z (1987).
Garzia et al, *Chemical Abstracts* 84:155677j (1976).
Gainer et al, *Chemical Abstracts* 75:85659t (1971).

(List continued on next page.)

*Primary Examiner*—Carlos Azpuru
*Attorney, Agent, or Firm*—Oblon, Spivak, McClelland, Maier & Neustadt, P.C.

[57] ABSTRACT

Vaginal application of cysteamine, cystamine, phosphocysteamine, or a pharmaceutically acceptable salt thereof is effective for contraception.

18 Claims, No Drawings

OTHER PUBLICATIONS

Sarin et al, *NATO ASI Ser.*, vol. 120, pp. 329–342 (1986).
Kalebic et al, *Proc. Natl. Acad. Sci. USA*, vol. 88, pp. 986–990 (1991).
Djurhuus et al, *Carcinogenesis*, vol. 12, pp. 241–247 (1991).
Shulof et al, *Arzneimittal Forschung*, vol. 36, pp. 1531–1534 (1986).
Kubota et al, *AIDS Research and Human Retroviruses*, vol. 6, pp. 919–927 (1990).
Oxford et al, *Chemical Abstracts* 78:119655t (1973).
*Chemical Abstracs* 85:28782k (1976).
Yamamoto et al, *Chemical Abstracts* 113:55076m (1990).
Wainberg et al, *Chemical Abstracts* 112:48337y (1990).
Michaels et al, *Chemical Abstracts* 117:258256a (1992).
Windholtz, "The Merck Index", 10th Edition, Published 1983 by Merck & Co., Inc., Items 2771, 2773, 2775 and 2776.
Bartsevich et al, *Chemical Abstracts* 113:55075k (1990).

METHODS, COMPOSITES AND ARTICLES FOR CONTRACEPTION

This is a continuation-in-part application of U.S. patent application Ser. No. 08/492,478, filed Jun. 22, 1995, now U.S. Pat. No. 5,646,189 which is a continuation of U.S. patent application Ser. No. 08/136,697, filed Oct. 15, 1993, now abandoned.

BACKGROUND OF THE INVENTION

1. Field of the Invention

The present invention relates to methods, compositions, and articles, effective for contraception.

2. Discussion of the Background

Currently, there are a number of pharmaceutical compositions available for use as contraceptive agents. For example, the contraceptive foam Semicid, contains non-ylphenoxypolyoxyethene glycol (nonoxynol-9) as a contraceptive agent. However, nonoxynol-9 is irritating to mucus membranes and can cause cervico-vaginal irritation. This irritation increases the risk of infections, because it causes a disruption of the vaginal and cervical epithelial cell integrity (see *Sex. Trans. Dis.*, vol. 18, p. 176 (1991)). Further studies have shown that nonoxynol-9 is not an effective anti-viral agent (see *J. Med. Primatol*, vol. 19, p. 401 (1990)). Thus, nonoxynol-9 is effective as a contraceptive agent but is irritating to the mucus membranes and serves to increase the risk of vital infection because of its irritant activity.

The drawbacks of conventional contraceptive agents, such as nonoxynol-9, are discussed extensively in U.S. Pat. Nos. 5,387,611 and 5,380,523, which are incorporated herein by reference.

Recently, interest has focused on the development of non-spermicidal contraceptive compositions. These efforts are based, in part, on the observed correlation between inhibition of acrosomal enzymes (e.g., acrosin and hyaluronidase) and contraception (see, e.g. A. S. Bourinbaiar et al, *Contraception*, vol. 51, pp. 319–322 (1995); J. S. Chen et al, *Zygote*, vol. 1, pp. 309–313 (1993); N. R. Moudgal et al, *J. Reprod. Fertil.*, vol. 96, pp. 91–102 (1992); and S. S. Majumdar et al, *Contraception*, vol. 41, pp. 641–653 (1990)). However, to date, no completely satisfactory contraceptive compound has been found.

Thus, there remains a need for methods, compositions, and articles useful for contraception which do not suffer from the drawbacks of conventional means of contraception.

SUMMARY OF THE INVENTION

Accordingly, it is one object of the present invention to provide novel methods for contraception.

It is another object of the present invention to provide novel methods for contraception which have a reduced tendency to suffer from the drawbacks of conventional methods.

It is another object of the present invention to provide novel compositions useful for contraception.

It is another object of the present invention to provide novel compositions useful for contraception which have a reduced tendency to suffer from the drawbacks of conventional contraceptive compositions.

It is another object of the present invention to provide novel articles useful for contraception.

It is another object of the present invention to provide novel articles useful for contraception which have a reduced tendency to suffer from the drawbacks of conventional contraceptive articles.

These and other objects, which will become apparent during the following detailed description, have been achieved by the inventor's discovery that cysteamine, cystamine, phosphocysteamine, and pharmaceutically acceptable salts thereof are effective contraceptives when topically applied to the vagina or incorporated into, e.g., vaginal suppositories, condom lubricants, vaginal foams, and other barrier-enhancing methods of contraception.

DETAILED DESCRIPTION OF THE PREFERRED EMBODIMENTS

Thus, in a first embodiment, the present invention relates to a method of contraception by the vaginal application of an effective amount of cysteamine, cystamine, phosphocysteamine, or a pharmaceutically acceptable salt thereof. Cysteamine is a known compound of the formula

Cysteamine may be prepared from ethanolamine and carbon disulfide via 2-mercaptothiazoline (Gabriel et al, *Ber.*, vol. 31, 2837 (1898); Knorr et al, *Ber.*, vol. 36, 1281 (1903); and Mills, Jr. et al, *J. Am. Chem. Soc.*, vol. 62, 1173 (1940)) or via ethyleneimine (Wenker, *J. Am. Chem. Soc.*, vol. 57, 2328 (1935); Mills, Jr. et al, *J. Am. Chem. Soc.*, vol. 62, 1173 (1940); and Shirley, *Preparation of Organic Intermediates*, Wiley, NY, p. 189 (1951)).

Cysteamine is useful for the treatment of nephropathic cystinosis (Thoene et al, *The Journal of Clinical Investigation*, vol. 58, pp. 180–189 (1976); Thoene et al, *The Journal of Pediatrics*, vol. 96, pp. 1043–1044 (1980); Thoene, in *Orphans Drugs and Orphan Diseases: Clinical Realities and Public Policy*, Alan R. Liss, NY, pp. 125–131 (1983); Thoene, in *Cooperative Approaches to Research and Development of Orphan Drugs*, Alan R. Liss, NY, pp. 157–162 (1985); Pisoni et al, *The Journal of Biological Chemistry*, vol. 260, pp. 4791–4798 (1985); Gahl et al, *New England Journal of Medicine*, vol. 316, pp. 971–977 (1987); and Smolin et al, *Pediatric Research*, vol. 23, pp. 616–620 (1988).

Cysteamine also shows good in vitro activity against HIV. When added twice-daily to cultures of CEM-T$_4$ lymphocytes, cysteamine at 100 μM shows excellent protection against HTLVIII$_B$ with treated cells showing 133% of control survival, and no toxicity (120.8% of control) (Thoene, J., *Clin. Res. Abstract*, May, 1992)). Experiments on other cell lines and with other HIV strains substantiate the antiviral effect of cysteamine against HIV and its lack of cellular toxicity at concentrations which completely inhibit the virus.

Cystamine has the formula

and may be prepared by the H$_2$O$_2$ oxidation of cysteamine (Mills, Jr. et al, *J. Am. Chem. Soc.*, vol. 62, 1173 (1940); and Barnett, *J. Chem. Soc.*, 1944, 5). Cystamine also demonstrates substantial activity against the HIV pathogen, and shows little cytotoxicity at 100 μM concentration.

Phosphocysteamine is the phosphorothioester of cysteamine and has the formula

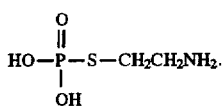

Phosphocysteamine is also known to be useful for the treatment of nephropathic cystinosis (Thoene et al, *The Journal of pediatrics*, vol. 96, pp. 1043–1044 (1980); Thoene, in *Cooperative Approaches to Research and Development of Orphan Drugs*, Alan R. Liss, NY, pp. 157–162 (1985); and Smolin et al, *Pediatric Research*, vol. 23, pp. 616–620 (1988)).

Cysteamine is known to be safe for use in humans and does not usually give rise to any frequent side-effects serious enough to require discontinuation of the drug. There is both in vitro and in vivo data about the safety of cysteamine when applied topically. Studies on the effect of cysteamine on the growth rate and cloning efficiency of epithelial fibroblasts show no effect on growth rate at concentrations up to 10 µM, but severe loss in cloning efficiency at that concentration. One hundred µM cysteamine caused an apparent two-fold increase in the doubling time and reduced the cloning efficiency to zero (Thoene, J., et al, *J. Clin. Invest*, vol. 58, pp. 180–189 (1976)). These in vitro experiments were performed using fibroblasts which are not protected as are cornified epithelial cells, in vivo, as found in the vaginal cavity.

More appropriate are the studies of topical cysteamine for use in the treatment of the keratitis of cystinosis. In this formulation, aqueous cysteamine at concentrations of 0.1% and 0.5%, which correspond to 10 mM and 50 mM, respectively, were used. These concentrations are effective in reducing the cystine crystals found in the corneas of patients with nephropathic cystinosis, and the drug is well-tolerated in chronic use via this modality. Rabbit studies have shown both concentrations to be safe as evaluated via the Draize test (Kaiser-Kupfer, M. et al, *Archives of Ophthalmology*, vol. 108, pp. 689–693 (1990); and Kaiser-Kupfer, M. et al, *New Eng. J. Med.*, vol. 316, pp. 775–779 (1987)).

Preferably, the present method involves the vaginal application of cysteamine or a pharmaceutically acceptable salt thereof.

Thus, the present method involves topical application to the vagina to prevent pregnancy as a result of vaginal intercourse. Typically, the topical application is carried out prior to the beginning of vaginal intercourse, suitably 0 to 60 minutes, preferably 0 to 5 minutes, prior to the beginning of vaginal intercourse. Suitably cysteamine is applied in an amount that will result in a local concentration of 1 mM to 1M, preferably 2.0 mM to 500 mM, most preferably 5 mM to 100 mM, throughout the vagina. In the case of cystamine, the suitable, preferred, and most preferred dosages correspond to the same respective dosages of cysteamine in terms of weight and one half those of cysteamine in terms of moles. In the case of phosphocysteamine, the suitable, preferred, and most preferred dosages are the same as those of cysteamine in terms of moles.

As will be made clear in the Examples below, the present compounds are effective as non-spermicidal contraceptives at low concentrations and exhibit spermicidal activity at higher concentrations.

The cysteamine may be applied to the vagina in a number of forms including aerosols, foams, jellies, creams, suppositories, tablets, tampons, etc. Compositions suitable for application to the vagina are disclosed in U.S. Pat. Nos. 2,149,240, 2,330,846, 2,436,184, 2,467,884, 2,541,103, 2,623,839, 2,623,841, 3,062,715, 3,067,743, 3,108,043, 3,174,900, 3,244,589, 4,093,730, 4,187,286, 4,283,325, 4,321,277, 4,368,186, 4,371,518, 4,389,330, 4,415,585, 4,551,148, 4,999,342, 5,013,544, 5,227,160, 5,229,423, 5,314,917, 5,380,523, and 5,387,611 which are incorporated herein by reference, and the present method may be carried out by applying cysteamine, cystamine, phosphocysteamine, or a pharmaceutically acceptable salt thereof to the vagina in the form of such a composition.

In some embodiments, it may be preferred to carry out the present method by vaginal application of cysteamine, cystamine, phosphocysteamine, or a pharmaceutically acceptable salt thereof without any additional non-spermicidal or spermicidal contraceptive agent. On the other hand, it may be preferred to coadminister an additional contraceptive agent, which may act either in a spermicidal or non-spermicidal way. Examples of such additional contraceptives include nonylphenoxypolyoxyethylene glycol (nonoxynol-9), benzethonium chloride, and chlorindanol.

It should be noted, however, that it is not necessary that a spermicidal active agent other than cysteamine, cystamine, phosphocysteamine, or a pharmaceutically acceptable salt thereof be present in the composition to effect impaired sperm viability. Rather, in some embodiments, no additional spermicidal agent need be present in the composition. Thus, at intravaginal concentrations higher than about 500 mM, cysteamine itself will exhibit spermicidal activity. The higher concentrations may provide a superior contraceptive effect by means of a combination of non-spermicidal and spermicidal contraception. At lower concentrations, the cysteamine, cystamine, phosphocysteamine, and/or pharmaceutically acceptable salt thereof are effective non-spermicidal contraceptives. As demonstrated in the Examples below, cysteamine has been found to be a potent inhibitor of hyaluronidase and acrosin.

While not intended to limit the present invention to any particular mechanism of action, the following explanations of the contraceptive effect of the present method are consistent with the experimental results presented in the examples below. Thus, when applied in an amount sufficient to result in a vaginal concentration of less than about 10 mM of cysteamine (or an equivalent amount of cystamine, phosphocysteamine, or pharmaceutically acceptable salt thereof), the primary mode of action could include hyaluronidase inhibition. At concentrations between about 10 mM and about 300 mM, the primary mode of action could include hyaluronidase inhibition and acrosin inhibition. At concentrations between about 300 mM and 1M, the primary mode of action could include inhibition of both hyaluronidase and acrosin, as well as spermicidal activity.

The composition containing the cysteamine, cystamine, phosphocysteamine or pharmaceutically acceptable salt thereof may be applied to the vagina in any conventional manner. Suitable devices for applying the composition to the vagina are disclosed in U.S. Pat. Nos. 3,826,828, 4,108,309, 4,360,013, and 4,589,880, which are incorporated herein by reference.

The present method also includes administration of mixtures of cysteamine, cystamine, phosphocysteamine, or salts thereof. For purposes of the present invention, the term pharmaceutically acceptable salt thereof refers to any salt of cysteamine, cystamine, or phosphocysteamine which is pharmaceutically acceptable and does not greatly reduce or inhibit the contraceptive effect of cysteamine, cystamine, or phosphocysteamine. Suitable examples include acid addition salts, with an organic or inorganic acid such as acetic acid, tartaric acid, trifluoroacetic acid, lactic acid, maleic acid, fumaric acid, citric acid, methanesulfonic acid, sulfuric acid, phosphoric acid, nitric acid, or hydrochloric acid. The use of trifluoroacetate, nitrate, or methanesulfonate salts in vaginal compositions may not be preferred due to irritation. In addition, for phosphocysteamine either or both of the hydrogen atoms on the phosphoryl group may be replaced with any suitable cation, such as $Na^+$, $K^+$, $Mg^{+2}$, $Ca^{++}$, $NH_4^+$, or $NR_4^+$ (where R is a $C_{1-4}$ alkyl).

It is to be further understood that the terms cysteamine, cystamine, phosphocysteamine, and pharmaceutically acceptable salts thereof include all the hydrated forms of these compounds as well as the anhydrous forms.

In another preferred embodiment, an antibacterial or antiviral agent may be coapplied to the vagina along with the cysteamine, cystamine, phosphocysteamine, and/or pharmaceutically acceptable salt thereof. Such antibacterial and antiviral agents are preferably those effective against sexually transmitted diseases and include butylurea (see U.S. Pat. No. 5,229,423, which is incorporated herein by reference) and benzalkonium chloride (see U.S. Pat. No. 5,387,611, which is incorporated herein by reference). The present invention also encompasses compositions and articles containing such antibacterial and/or antiviral agents.

The present invention also provides compositions useful for preventing pregnancy. As noted above, such compositions may be in the form of foams, creams, jellies, suppositories, tablets, aerosols, etc. Particularly preferred are vaginal suppositories. The concentration of cysteamine, cystamine, phosphocysteamine, or pharmaceutically acceptable salt in the composition is such to achieve the local vaginal concentrations described above upon administration of the usual amount of the type of composition being applied.

In this regard, it is noted that when the composition is in the form of a vaginal suppositories, the suppository will usually be 1 to 5 grams, preferably about 3 grams, and the entire suppository will be applied. A vaginal tablet will suitably be 1 to 5 grams, preferably about 2 grams, and the entire tablet will be applied. When the composition is a vaginal cream, suitably 0.1 to 2 grams, preferably about 0.5 grams of the cream will be applied. When the composition is a water-soluble vaginal cream, suitably 0.1 to 2 grams, preferably about 0.6 grams, are applied. When the composition is a vaginal spray-foam, suitably 0.1 to 2 grams, preferably about 0.5 grams, of the spray-foam are applied. When the composition is a vaginal soluble waffle, suitably the waffle is 0.1 to 2 grams, preferably about 0.3 grams, and the entire waffle is applied.

In some applications, it may be preferred that the composition also contain a spermicide. Examples of suitable spermicides are disclosed in the U.S. Patents cited and incorporated herein by reference above. Preferred spermicides include nonoxynol 9, benzethonium chloride, and chlorindanol. Suitably, the pH of the composition is 4.5 to 8.5. Vaginal compositions preferably have a pH of 4.5 to 6, most preferably about 5. In the case of phosphocysteamine, the pH is preferably about 7.

It may be preferred to include in the composition an agent which will mask the taste and/or odor of the cysteamine, cystamine, phosphocysteamine, and/or pharmaceutically acceptable salt thereof. Such agents include those flavoring agents and scents typically found in compositions intended for vaginal application, such as cinnamon or peppermint oil.

The present compositions may also be in the form of a time-release composition. In this embodiment, cysteamine, cystamine, phosphocysteamine, and/or a pharmaceutically acceptable salt thereof is incorporated in a composition which will release cysteamine, cystamine, phosphocysteamine, and/or a pharmaceutically acceptable salt thereof at a rate which will result in the vaginal concentration described above. Time-release compositions are disclosed in *Controlled Release of Pesticides and Pharmaceuticals*, D. H. Lew, Ed., Plenum Press, New York, 1981; and U.S. Pat. Nos. 5,185,155; 5,248,700; 4,011,312; 3,887,699; 5,143,731; 3,640,741; 4,895,724; 4,795,642; Bodmeier et al, *Journal of Pharmaceutical Sciences*, vol. 78 (1989); Amies, *Journal of pathology and Bacteriology*, vol. 77 (1959); and Pfister et al, *Journal of Controlled Release*, vol. 3, pp. 229–233 (1986), all of which are incorporated herein by reference. It should also be understood that when the time-release composition contains either cysteamine or phosphocysteamine, it may be desirable to include in the time-release composition an agent which is capable of converting cystamine or phosphocysteamine into cysteamine. In the case of cystamine, the agent may be any reducing agent capable of converting cystamine to cysteamine, such as glutathione. In the case of phosphocysteamine, the agent could be any phosphatase capable of converting phosphocysteamine to cysteamine and which retains its activity in the local environment (vagina) such as bovine or human prostatic acid phosphatase or alkaline phosphatase. The use of prostatic acid phosphatase is preferred.

The present compositions may also be in the form which releases cysteamine, cystamine, phosphocysteamine, and/or a pharmaceutically acceptable salt thereof in response to some event such as vaginal intercourse. For example, the composition may contain cysteamine, cystamine, and/or phosphocysteamine in vesicles or liposomes which are disrupted by the mechanical action of intercourse. Compositions comprising liposomes are described in U.S. Pat. No. 5,231,112 and Deamer and Uster, "Liposome Preparation: Methods and Mechanisms", in *Liposomes*, pp. 27–51 (1983); Sessa et al, *J. Biol. Chem.*, vol. 245, pp. 3295–3300 (1970); *Journal of Pharmaceutics and Pharmacology*, vol. 34, pp. 473–474 (1982); and *Topics in Pharmaceutical Sciences*, D. D. Breimer and P. Speiser, Eds., Elsevier, New York, pp. 345–358 (1985), which are incorporated herein by reference. Again, in the case of cystamine and phosphocysteamine, it may be desirable to include in the composition an agent which will convert the released cystamine and/or phosphocysteamine to cysteamine.

It should also be realized that the present compositions may be associated with an article, such as an intrauterine device (IUD), vaginal diaphragm, vaginal sponge, pessary, condom, etc. In the case of an IUD or diaphragm, time-release and/or mechanical-release compositions may be preferred, while in the case of condoms, mechanical-release compositions are preferred.

In another embodiment, the present invention provides novel articles which are useful for the prevention of pregnancy. In particular, the present articles are those which release cysteamine, cystamine, phosphocysteamine, and/or a pharmaceutically acceptable salt thereof when placed in the vagina. As in the case of the above-described compositions, it may be preferred that the present articles also release an agent capable of converting cystamine or phosphocysteamine into cysteamine. Thus, the present invention provides IUDs, vaginal diaphragms, vaginal sponges, pessaries, or condoms which contain or are associated with cysteamine, cystamine, phosphocysteamine, and/or a pharmaceutically acceptable salt thereof or a composition containing cysteamine, cystamine, phosphocysteamine, and/or a pharmaceutically acceptable salt thereof.

Thus, the present article may be an IUD which contains cysteamine, cystamine, phosphocysteamine, and/or a pharmaceutically acceptable salt thereof. Suitable IUDs are disclosed in U.S. Pat. Nos. 3,888,975 and 4,283,325 which are incorporated herein by reference.

The present article may be an intravaginal sponge which comprises and releases, in a time-controlled fashion, cysteamine, cystamine, phosphocysteamine, and/or a pharmaceutically acceptable salt thereof. Intravaginal sponges are disclosed in U.S. Pat. Nos. 3,916,898 and 4,360,013, which are incorporated herein by reference. The present article may also be a vaginal dispenser which releases cysteamine, cystamine, phosphocysteamine, and/or a pharmaceutically acceptable salt thereof. Vaginal dispensers are disclosed in U.S. Pat. No. 4,961,931, which is incorporated herein by reference.

The present article may also be a condom which is coated with cysteamine, cystamine, phosphocysteamine, and/or a pharmaceutically acceptable salt thereof. In a preferred embodiment, the condom is coated with a lubricant or penetration enhancing agent which comprises cysteamine, cystamine, phosphocysteamine, and/or a pharmaceutically acceptable salt thereof. In a particularly preferred embodiment, the lubricant or penetration enhancing agent comprises cysteamine, cystamine, phosphocysteamine, and/ or a pharmaceutically acceptable salt thereof which is encapsulated in liposomes such that the cysteamine, cystamine, phosphocysteamine, and/or a pharmaceutically acceptable salt thereof is released from the liposomes upon intercourse. Lubricants and penetration enhancing agents are described in U.S. Pat. Nos. 4,537,776; 4,552,872; 4,557,934; 4,130,667, 3,989,816; 4,017,641; 4,954,487; 5,208,031; and 4,499,154, which are incorporated herein by reference. In another preferred embodiment, cysteamine, cystamine, phosphocysteamine, and/or a pharmaceutically acceptable salt thereof is contained inside the condom. In a particularly preferred embodiment, cysteamine, cystamine, phosphocysteamine, and/or a pharmaceutically acceptable salt thereof is contained in a reservoir in the tip of the condom.

Other features of the invention will become apparent in the course of the following descriptions of exemplary embodiments which are given for illustration of the invention and are not intended to be limiting thereof.

EXAMPLES

I. Compositions

Some examples are herebelow given relating to compositions according to the invention, which contain cysteamine.

1. Vaginal Suppositories
Composition for a 3-gram suppository:

|  |  |
|---|---|
| Cysteamine | 0.005 g |
| Hexantriol | 0.1 g |

Polyglycol 1500 balance to 3

2. Vaginal Tablets
Composition for a 2-gram tablet:

|  |  |
|---|---|
| Cysteamine | 0.004 g |
| Anhydrous citric acid | 0.7 g |
| Sodium bicarbonate | 0.3 g |
| Polyglycol 6000 | 0.4 g |

Lactose balance to 2 g

3. Vaginal Cream
Percentage composition:

|  |  |
|---|---|
| Cysteamine | 1 g |
| Nonionic autoemulsifying base | 4 g |

Water balance to 100 g
for each application, 0.5 grams of the cream are vaginally administered with a suitable syringe.

4. Water-soluble Vaginal Cream
Percentage compositions:

|  |  |
|---|---|
| Cysteamine | 1 g |
| Polyglycol 400 | 30 g |
| Polyglycol 6000 | 8.5 g |
| Hexantriol | 3 g |

Water balance to 100 g
For each application, 0.6 grams of the cream are vaginally administered with a suitable syringe.

5. Vaginal Spray-foam
Percentage composition:

|  |  |
|---|---|
| Cysteamine | 1 g |
| Polyglycol 6000 | 2 g |
| Nonionic emulsifying agent | 2 g |
| Water | 85 g |
| Freon 12/144 (70.30) | 10 g |

For each application, 0.5 grams of the foam are vaginally administered.

6. Vaginal Soluble Waffle
Composition for one 0.340-gram waffle:

|  |  |
|---|---|
| Cysteamine | 0.003 g |
| Starch | 0.040 g |
| Water-soluble lanolin | balance to 0.340 g |

7. Vaginal Suppository

| Components | Percent by weight |
|---|---|
| polyethylene glycol 1000 | 65.0 |
| polyethylene glycol 300 NF | 3.0 |
| cellulose | 1.0 |
| alginic acid (80 mesh) | 15.0 |
| sodium bicarbonate (100 mesh) | 12.0 |
| Cysteamine | 4.0 |

This composition is prepared as follows. The two polyethylene glycols are melted together at a temperature of about 62°–68° C. When the melt is complete, the cysteamine is added to the melt under an atmosphere of $N_2$ with agitation, the agitation being continued for sufficient time to totally mix the ingredients, usually from about 5 to 10 minutes. The cellulose is then dispersed into the mixture under slow-speed agitation, after which first the sodium bicarbonate and then the alginic acid is added. Agitation is continued for about 15 to 30 minutes to completely disperse the latter ingredients into the mixture. During this period, the temperature is maintained substantially constant. Thereafter, the mass is cooled to about 52° C. and is then poured in torpedo-shaped molds which have been pre-chilled to about 15°–20° C. The molds are then placed in freezing cabinets until the mass is thoroughly chilled. The products are thereafter removed from the molds, ready for use or storage.

8. Vaginal Suppository

| Components | Percent by weight |
| --- | --- |
| polyethylene glycol 1000 | 53.0 |
| polyethylene glycol 300 | 11.7 |
| cellulose | 1.0 |
| methyl cellulose | 1.0 |
| alginic acid | 16.7 |
| sodium bicarbonate | 13.3 |
| Cysteamine | 3.3 |

The above ingredients are mixed together in the manner described in Example I-7 and treated at the temperature and for the periods described in Example I-7.

9. Vaginal Gel

| | Percent by wt/vol. |
| --- | --- |
| Cysteamine | 1 |
| Poloxamer-407-(Pluronic F-127) (MW 11,500) | 18 |
| PEG 400 | 20 |
| Glycerin | 20 |
| Polysorbate 60 | 3 |
| BHA | .02 |
| Water qs ad | 100 |

The composition is prepared by mixing all the ingredients under an atmosphere of $N_2$ with approximately 90% of the required water and allowing the polyoxyethylene-polyoxypropylene block copolymer to hydrate and completely dissolve with gentle stirring. When a clear gel is obtained, the remaining water is added to adjust the volume to 100 ml.

II. Biological Activity

1. Hyaluronidase Inhibition

Hyaluronidase Inhibition Assay

Hyaluronidase activity is quantified by measuring the extent of hyaluronic acid hydrolysis. This is measured by determining the concentration of N-acetylglucosamine-reactive material, resulting from enzyme action.

Reaction mixtures contain the following, in a total volume of 0.25 ml: 0.1M sodium acetate, containing 0.15M NaCl, pH 5.5 (Acetate buffer); 7.2 Units sheep testicular hyaluronidase (Sigma, Type III; cat. no. H-2251), from a stock solution dissolved in the Acetate buffer; 0.3 mg/ml hyaluronic acid (Sigma, from bovine vitreous humor, cat-no. H-7630).

The test compound is screened at a concentration of 1 mg/ml, unless aqueous solubility is limited. The enzyme is preincubated with the test agent for 10 minutes prior to starting the reaction by adding hyaluronic acid. Enzyme reactions are determined by the method of Aronson and Davidson (*J. Biol. Chem.*, vol. 242, pp. 437–440 (1967)). Incubations are carried out for 30 minutes at ambient temperature. Reaction product is determined colorimetrically after reaction with p-dimethylaminobenzaldehyde (Reissig et al., *J. Biol. Chem.*, vol. 217, pp. 959–966 (1955)). The absorbance of the resultant adduct is immediately determined at 545 nm.

Differences are determined between absorbencies for reactions run in the presence and absence of hyaluronidase (blank, in which hyaluronidase is added after terminating reaction). This is compared to a standard curve of known amounts of N-acetylglucosamine that were treated identically to enzyme reaction mixtures, and converted to µmole equivalents of N-acetylglucosamine. The data are reported as % inhibition, compared to control. A dose-response curve is generated at several concentrations of test compound if significant inhibition is obtained at the screening concentration.

$IC_{50}$ values (those concentrations of inhibitor that produce 50% inhibition under the conditions of the assay) are determined by analyzing enzyme activity as a function of inhibitor concentration, with curve-fitting software (TableCurve 2D, version 3.02; Jandel Scientific).

Results

Using this assay, cysteamine was found to completely inhibit testicular hyaluronidase at a concentration of 1 mg/ml. The results are shown in the tables below:

Efficacy of Test Agents as Hyaluronidase Inhibitors

| Compound | % Inhibition at 1 mg/ml | $IC_{50}$ |
| --- | --- | --- |
| cysteamine | 100 | 151 µg/ml |
| nonoxynol-9 | 4 | — |

Determination of Dose-Response for Hyaluronidase Inhibition by Cysteamine

| Cysteamine (µg/ml) | Absorbance at 545 nm | |
| --- | --- | --- |
| | Blank* | Reaction |
| 0 | 0.0463** | 0.1921 |
| 1.6 | 0.0463** | 0.1892 |
| | | 0.1967 |
| 8.0 | 0.0463** | 0.1955 |
| | | 0.1853 |
| 40.0 | 0.0463** | 0.1775 |
| | | 0.1855 |
| 200 | 0.0463** | 0.0585 |
| | | 0.0656 |
| 1,000 | 0.0463** | 0.0068 |
| | | 0.0069 |
| TableCurve Equation | 8012 | |
| Coefficient of Determination ($r^2$) | 1.000 | |
| $IC_{20}$ | 87 µg/ml | |
| $IC_{50}$ | 151 µg/ml | |
| $IC_{80}$ | 219 µg/ml | |

*Blanks received hyaluronidase after adding borate buffer and NaOH to the tubes (after the 30 minute incubation).
**This value is the average of all blank values, as follows: absorbance readings were 0.0376, 0.0514, 0.0507, 0.0415 and 0.0497 for blanks containing 0, 1.6, 8, 40, 200 and 1,000 µg/ml cysteamine, respectively.

2. Acrosin Inhibition

Acrosin Inhibition Assay

Human acrosin activity is measured by following the progression of hydrolysis of N-α-benzoyl-L-arginine ethyl ester (BAEE) spectrophotometrically at 253 nm. Enzyme isolation, partial purification and measurement are carried out by methods described in detail by Anderson et al. (*Biochem. J.*, vol. 199, pp. 307–316 (1981)). Briefly, human acrosin is isolated from washed spermatozoa from frozen semen by extraction with 66 mM acetic acid, pH 2.8. The extract is concentrated by ultrafiltration (Amicon PM 10) and applied to a column that contains Sephadex G-150 (superfine); elution is carried out with 55 mM acetic acid that contains 0.1M NaCl. The eluted volume that contains acrosin activity is pooled and used as the source of enzyme.

Enzyme reaction mixtures contain the following: 50 mM sodium phosphate, pH 7.5 (Anderson et al, *Arch. Biochem. Biophys.*, vol. 241, pp. 509–520 (1985)); Enzyme-containing protein (3–5 mIU, where 1 mIU is the amount of enzyme required to hydrolyze 1 nmole BAEE per min); 0.05 mM BAEE; with or without inhibitor, in a total volume of 1.0 ml.

The test compound is screened at a concentration of 1 mg/ml, unless solubility is limited. The enzyme is preincubated with the test agent for 5 minutes prior to starting the reaction by adding BAEE. Reaction blanks, in which either substrate or enzyme has been eliminated, are run in parallel to the reactions.

The rate of change in absorbance at 253 nm is determined. The change in absorbance that corresponds to 1 µmole of BAEE (in a total volume of 1.0 ml) hydrolyzed is taken as 1.15.

The enzyme activity in the presence of each agent is compared with that for the control reaction (no test agent added). The data are reported as % inhibition. Compounds that show no activity at the screening concentration of 1 mg/ml are considered to be inactive. A dose-response curve is generated at several concentrations of test compound if significant inhibition is obtained at the screening concentration.

Reversibility of acrosin inhibition is determined by the method of Ackermann and Potter (*Proc. Soc. Exp. Biol. Med.*, vol. 72, pp. 1–9 (1949)), in which the level of inhibited enzyme activity is determined in the presence of different amounts of enzyme. The data so obtained are consistent with a reversible mechanism of inhibition of human acrosin by cysteamine.

$IC_{50}$ values (those concentrations of inhibitor that produce 50% inhibition under the conditions of the assay) are determined by analyzing enzyme activity as a function of inhibitor concentration, with curve-fitting software (TableCurve 2D, version 3.02; Jandel Scientific).

Results

Using this procedure, cysteamine has been screened as an acrosin inhibitor and was found to be active. The results are shown in the table below:

| Inhibition of Human Acrosin by Cysteamine | |
|---|---|
| Cysteamine (mg/ml) | Acrosin Activity (µmoles BAEE hydrolyzed/min/mg protein)[A] |
| 0 | 5.4 ± 0.14 (21) |
| 0.08 | 5.2 ± 0.74 (2) |
| 0.10 | 3.8 ± 0.32 (2) |
| 0.25 | 3.4 ± 0.10 (2) |
| 0.50 | 2.2 (n = 1) |
| 0.8 | 0.9 ± 0.28 (2) |
| 1.0 | 0.6 (n = 1) |
| TableCurve Equation | 8011 |
| Coefficient of Determination ($r^2$) | 0.997 |
| $IC_{20}$ | 0.12 mg/ml |
| $IC_{50}$ | 0.37 mg/ml |
| $IC_{80}$ | 0.82 mg/ml |
| 3 Log reduction (99.9% inhibition) | 3.27 mg/ml |

[A]All activities have been adjusted to a control (no inhibitor) specific activity of 10.00 µmoles BAEE hydrolyzed per min per mg protein. Specific activity was measured in the presence of saturating concentration of BAEE (substrate; 0.5 mM). Assays that were run to determine the $IC_{50}$ value of cysteamine as an acrosin inhibitor were run in the presence of 0.05 mM cysteamine so as to increase the probability of detecting inhibition, independent of the mechanism of action. Enzyme was preincubated in the presence of cysteamine for 5 minutes at ambient temperature before initiating the reaction with substrate. In all instances, reaction times = 4.0 minutes. Values are expressed as averages ± standard errors of the mean, with the number of determinations that were used in the calculated values indicated in parentheses.

3. Spermicidal Activity

Assessment of Spermicidal Activity

The method is based on that originally described by Sander and Cramer (F. V. Sander and S. D. Cramer. *Human Fertil.*, vol. 6, pp. 134 (1941)). Apparent spermicidal activity of the test agents are compared to that of a control preparation of nonoxynol-9 (N9).

For the screening of spermicidal activity of a test agent, a solution of 50 mg/ml is prepared in 0.9% NaCl. This solution is adjusted to pH 7.0 with either HCl or NaOH and is further diluted in 0.9% NaCl to concentrations of 25 mg/ml, 10 mg/ml, 5 mg/ml, and 2.5 mg/ml. N9 is prepared as a solution of 100 µg/ml in 0.9% NaCl.

The agents are tested by mixing 40 µl of freshly ejaculated semen with 200 µl of test agent at each concentration. Just prior to and 30 seconds after mixing, the percentage of motile spermatozoa is determined by microscopic observation (400×). If 90–100% inhibition of motility is obtained at the lowest concentration tested, the experiment is repeated with a different range of concentrations, the highest concentration being 2.5 mg/ml. A dose-response curve is constructed.

The test outcome is reported as the concentration of agent in the semen sample that reduces motility by 50% and where possible, the lowest concentration of agent that (virtually) completely inhibits motility.

Results

Using this procedure, cysteamine was found to reduce sperm motility. Although cysteamine was found to be less effective than nonoxynol-9 as a spermicide on a weight basis, cysteamine may be used in high amounts, because it is well tolerated (see results on the effects on normal vaginal flora below). Thus, cysteamine may be used as a spermicide at higher concentrations.

| Efficacy of Contraceptives as Spermicidal Agents | |
|---|---|
| Compound | $IC_{50}$ |
| cysteamine | 15.5 mg/ml |
| nonoxynol-9 | 62 µg/ml |

4. Effects on Normal Vaginal Flora

Cysteamine was screened with regard to its potential cytotoxicity toward normal vaginal flora. Growth of vaginal lactobacillus was used as a measure of this effect.

Assay of Vaginal Lactobacillus Growth

*Lactobacillus gasseri*, obtained from the American Type Culture Collection (Rockville, Md.) is cultured under anaerobic conditions at 37° in the presence of test agent or no additions (control). Beginning at 120 minutes after the start of incubation and at 20 minute intervals, for a total length of 240 minutes, samples are removed from the incubation flasks, and the absorbance of each suspension at 550 nm is determined, as an estimate of cell density. Data are fit to the equation, Ln (Absorbance)=a+b (Time), where a is the absorbance at 0 time, b is the slope of the curve, and time is measured in minutes. The doubling time ($T_D$) is calculated from the equation $T_D$=(Ln 2)/b. Values are given as the doubling time of bacterial growth, together with the 90% confidence limits. Inhibition of bacterial growth by a test agent can be directly calculated from the reciprocal values of the doubling time (i.e., 75% inhibition of the reciprocal of the calculated doubling time is equal to 75% inhibition of bacterial growth).

Dose-response curves are produced by determining the doubling time of the culture in the presence of each of several concentrations of test agent, the exact range of which is determined by the results of the screening test that is described above. The concentration of test agent that inhibits the growth of lactobacillus by 50% ($IC_{50}$) is determined from the calculated doubling time at each concentration of test agent, with curve-fitting software (TableCurve 2D, version 3.02, Jandel Scientific).

Results

Using this assay, cysteamine had no effect on the propagation of lactobacillus at a concentration of 5 mg/ml, indicating that it would be well tolerated in humans for this usage.

Ability of Test Agents to Inhibit Growth of Vaginal Lactobacillus

| Compound | % Inhibition at 5 mg/ml | $IC_{50}$ (mg/ml) |
| --- | --- | --- |
| cysteamine | 0 | — |
| nonoxynol-9 | 60** | 0.4 mg/ml |

**Tested at 0.5 mg/ml

Summary of Biological Properties of Cysteamine

| | | | |
| --- | --- | --- | --- |
| Contraceptive, in vitro | Acrosin Inhibitor | Yes | $IC_{50}$ = 370 µg/ml; 3-Log reduction at 3.3 mg/ml |
| | Hyaluronidase Inhibitor | Yes | $IC_{50}$ = 151 µg/ml |
| | Spermicide | Yes | $IC_{50}$ = 15.5 mg/ml |
| Safety | Normal Vaginal Flora | No inhibition of lactobacillus at 5 mg/ml | Tested at 5 mg/ml |

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A method of contraception, comprising topical application of an effective amount of a compound selected from the group consisting of cysteamine, cystamine, phosphocysteamine, and pharmaceutically acceptable salts thereof, to a subject in need thereof.

2. The method of claim 1, wherein said compound is cysteamine.

3. The method of claim 1, wherein said topical application is vaginal application.

4. The method of claim 3, wherein said compound is cysteamine.

5. The method of claim 1, comprising coadministration of a spermicide.

6. The method of claim 5, wherein said compound is cysteamine.

7. A pharmaceutical composition for contraception, comprising (a) an effective amount of a compound selected from the group consisting of cysteamine, cystamine, phosphocysteamine, and pharmaceutically acceptable salts thereof, (b) a spermicide, and (c) a pharmaceutically acceptable carrier, said composition being in a form suitable for topical application.

8. The pharmaceutical composition of claim 7, wherein said compound is cysteamine.

9. The pharmaceutical composition of claim 7, wherein said compound is cysteamine.

10. The pharmaceutical composition of claim 7, which is in the form of a foam, jelly, cream, tablet, or pessary.

11. The pharmaceutical composition of claim 10, wherein said compound is cysteamine.

12. The pharmaceutical composition of claim 7, which is in the form of a vaginal suppository.

13. The pharmaceutical composition of claim 12, wherein said compound is cysteamine.

14. An article, comprising a substrate and a compound selected from the group consisting of cysteamine, cystamine, phosphocysteamine, and pharmaceutically acceptable salts thereof, said article being suitable for insertion in a vagina and wherein said article releases a contraceptive-effective amount of said compound when inserted into said vagina, wherein said article is an IUD, vaginal diaphragm, vaginal sponge, pessary, or condom.

15. The article of claim 14, wherein said compound is cysteamine.

16. The article of claim 14, wherein said compound is cysteamine.

17. The article of claim 14, which is a condom and wherein said compound is comprised in a lubricant on a surface of said condom.

18. The article of claim 17, wherein said compound is cysteamine.

* * * * *

UNITED STATES PATENT AND TRADEMARK OFFICE
CERTIFICATE OF CORRECTION

PATENT NO. : 5,725,870
DATED : March 10, 1998
INVENTOR(S) : Jess G. THOENE

It is certified that error appears in the above-identified patent and that said Letters Patent is hereby corrected as shown below:

On the title page, item [54] and on top of column 1, the word COMPOSITES should be:

--COMPOSITIONS--

Signed and Sealed this

Second Day of June, 1998

Attest:

BRUCE LEHMAN

Attesting Officer

Commissioner of Patents and Trademarks